US012566145B2

(12) United States Patent
Zhang et al.

(10) Patent No.: US 12,566,145 B2
(45) Date of Patent: Mar. 3, 2026

(54) DIGITAL RADIOGRAPHY SYSTEM AND DIGITAL RADIOGRAPHY METHOD

(71) Applicants: Nuctech Company Limited, Beijing (CN); Tsinghua University, Beijing (CN)

(72) Inventors: Li Zhang, Beijing (CN); Yunda Sun, Beijing (CN); Xin Jin, Beijing (CN); Wuyang Liang, Beijing (CN); Zhenhua Zhao, Beijing (CN); Kemin Hu, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 172 days.

(21) Appl. No.: 18/574,706

(22) PCT Filed: Jul. 4, 2022

(86) PCT No.: PCT/CN2022/103739
§ 371 (c)(1),
(2) Date: Dec. 27, 2023

(87) PCT Pub. No.: WO2023/280125
PCT Pub. Date: Jan. 12, 2023

(65) Prior Publication Data
US 2024/0319113 A1    Sep. 26, 2024

(30) Foreign Application Priority Data
Jul. 7, 2021    (CN) .......................... 202110768526.4

(51) Int. Cl.
*G01N 23/04* (2018.01)
*A61B 6/00* (2006.01)

(52) U.S. Cl.
CPC ................ *G01N 23/04* (2013.01); *A61B 6/52* (2013.01); *G01N 2223/401* (2013.01)

(58) Field of Classification Search
CPC .... G01N 23/04; G01N 2223/401; A61B 6/52; G01V 5/22
See application file for complete search history.

(56) References Cited

U.S. PATENT DOCUMENTS 5,293,312 A    3/1994    Waggener
7,302,035 B2    11/2007    Hu et al.
(Continued)

FOREIGN PATENT DOCUMENTS

CN    1779447 A    5/2006
CN    201199234    2/2009
(Continued)

OTHER PUBLICATIONS

"CN Publication No. 202110768526.4 First Office Action mailed Feb. 27, 2024", with English translation, 18 pages.
(Continued)

*Primary Examiner* — Kiho Kim
(74) *Attorney, Agent, or Firm* — Schwegman Lundberg & Woessner, P.A.

(57) ABSTRACT

A digital radiography system and a digital radiography method. The digital radiography system includes: detectors (L) mounted on a plurality of detector arm supports (L1, L2) formed in a first plane (P); and a ray source (S) that is non-coplanar with the first plane (P). The digital radiography system further includes an image processing apparatus (10).

18 Claims, 6 Drawing Sheets

<u>100</u>

(56) References Cited

U.S. PATENT DOCUMENTS

| | | | |
|---|---|---|---|
| 9,693,749 | B2 | 7/2017 | Ni et al. |
| 2006/0203962 | A1 | 9/2006 | Hu et al. |
| 2007/0081623 | A1 | 4/2007 | Eilbert |
| 2007/0140415 | A1 | 6/2007 | Garms et al. |
| 2009/0147913 | A1 | 6/2009 | Dragon et al. |
| 2010/0020921 | A1 | 1/2010 | Dong et al. |
| 2015/0204989 | A1 | 7/2015 | Ni et al. |
| 2017/0108453 | A1* | 4/2017 | Foland ................. G01N 23/046 |
| 2017/0205360 | A1 | 7/2017 | Cinquin et al. |
| 2017/0251995 | A1 | 9/2017 | Ni et al. |
| 2019/0137651 | A1 | 5/2019 | Bendahan |
| 2019/0204240 | A1 | 7/2019 | Li et al. |
| 2020/0022669 | A1 | 1/2020 | Ni et al. |
| 2021/0030389 | A1 | 2/2021 | Yardi et al. |

FOREIGN PATENT DOCUMENTS

| | | | |
|---|---|---|---|
| CN | 101398397 | | 4/2009 |
| CN | 102230975 | | 11/2011 |
| CN | 104749198 | | 7/2015 |
| CN | 104783824 | A | 7/2015 |
| CN | 106706675 | | 5/2017 |
| CN | 106706681 | | 5/2017 |
| CN | 109681738 | A | 4/2019 |
| CN | 110006931 | A | 7/2019 |
| CN | 110988974 | A | 4/2020 |
| CN | 111221049 | | 6/2020 |
| DE | 102007045798 | | 4/2009 |
| DE | 102011084683 | | 4/2013 |
| EP | 2713156 | A1 | 4/2014 |
| FR | 3024235 | | 1/2016 |
| JP | 2003222676 | A | 8/2003 |
| JP | 2016064119 | | 4/2016 |
| RU | 2015106330 | | 9/2016 |
| WO | WO-2023280125 | A1 | 1/2023 |

OTHER PUBLICATIONS

"CN Publication No. 202110768526.4 Notification to Grant mailed Feb. 27, 2024", with English translation, 6 pages.

Fang, Zheng, "Method of el iminating the fracture artifact of twin CCD detector CT with English abstract", Optical Technique vol. 33 No. 6, (Nov. 2007), 4 pages.

Huang, Qiuhong, "Study on the geometric calibration method for static cone-beam CT imaging system with English abstract", Chinese Journal of Scientific Instrument vol. 36 No. 10, (Oct. 2015), 8 pages.

Kong, Wei-Wu, "Correction Method for Deformation Image of Channel Type Security Inspection Equipment Based on Imaging Scale Consistency with English Abstract", Digital Technology and Application vol. 38 No. 9, (Sep. 2020), 3 pages.

Lv, Shaojie, "Fast C-arm projection image correction based on visual model with English abstract", Gaoji Mutongxun vol. 20 Issue 1, (Jan. 2010), 5 pages.

Zeng, Jian-Bin, "New method for geometry calibration of digital breast tomosynthesis system with English abstract", Journal of Shenyang University of Technology vol. 37 No. 5, (Sep. 2015), 6 pages.

"European Application No. 22836876.7, Extended European Search Report dated May 22, 2025", (May 22, 2025), 8 pgs.

"International Application No. PCT/CN2022/103739, Search Report mailed Sep. 14, 2022", (Sep. 14, 2022), 7 pgs.

"International Application No. PCT/CN2022/103739, Written Opinion mailed Sep. 14, 2022", (Sep. 14, 2022), 7 pgs.

Ding, Liyong, et al., "Box-Type Detection and Scanning Subsystem of Container Checking System", Hoisting and Conveying Machinery, ISSN: 1001-0785, (Dec. 31, 2010), 75-76.

* cited by examiner

100

200 image processing apparatus 10 projection acquisition portion
101 time deviation correction portion
102 space deviation correction
portion 103

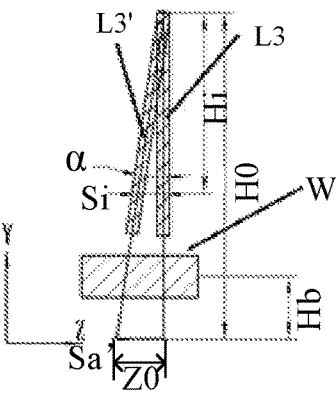

Fig. 5

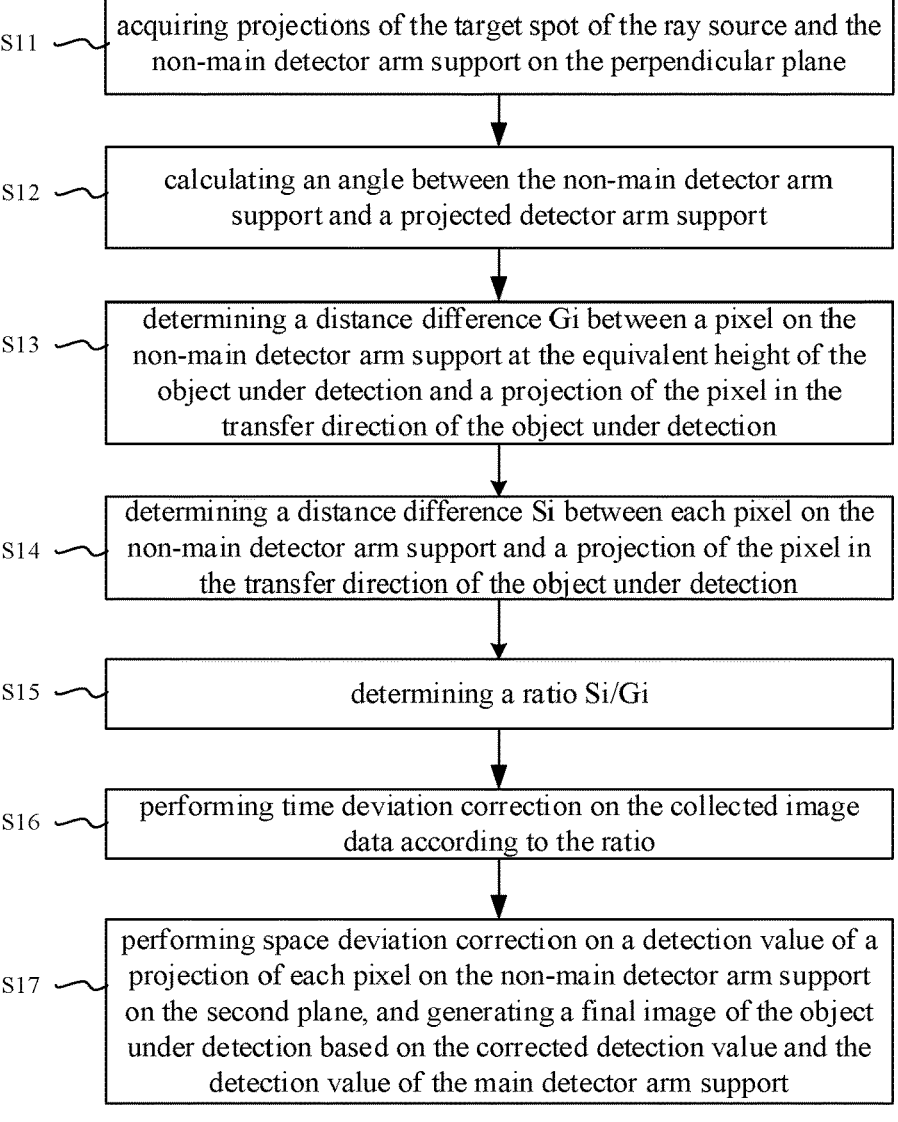

S11 — acquiring projections of the target spot of the ray source and the non-main detector arm support on the perpendicular plane S12 — calculating an angle between the non-main detector arm support and a projected detector arm support S13 — determining a distance difference Gi between a pixel on the non-main detector arm support at the equivalent height of the object under detection and a projection of the pixel in the transfer direction of the object under detection S14 — determining a distance difference Si between each pixel on the non-main detector arm support and a projection of the pixel in the transfer direction of the object under detection S15 — determining a ratio Si/Gi S16 — performing time deviation correction on the collected image data according to the ratio S17 — performing space deviation correction on a detection value of a projection of each pixel on the non-main detector arm support on the second plane, and generating a final image of the object under detection based on the corrected detection value and the detection value of the main detector arm support

Fig. 6

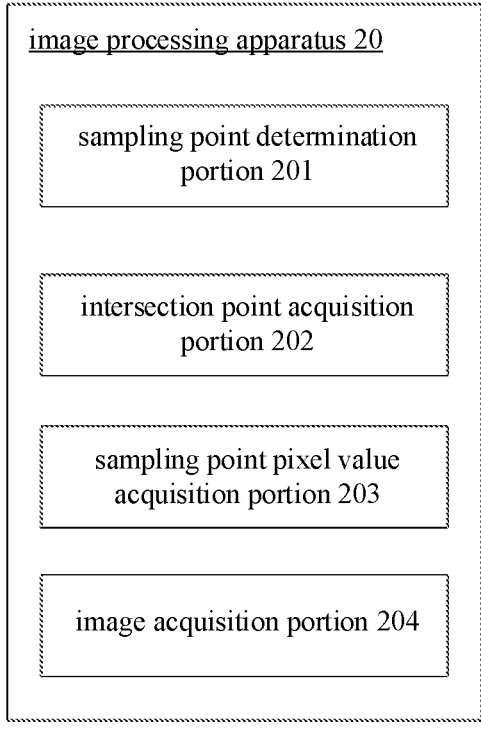

image processing apparatus 20 sampling point determination portion 201 intersection point acquisition portion 202 sampling point pixel value acquisition portion 203 image acquisition portion 204

Fig. 9

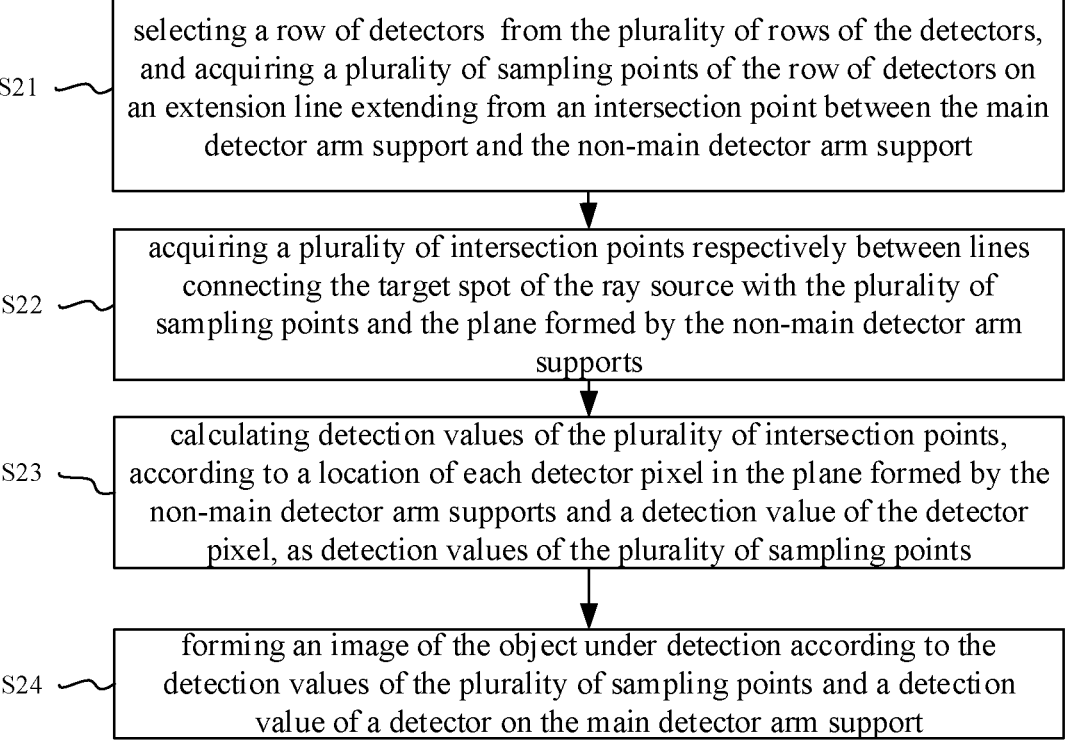

S21 — selecting a row of detectors from the plurality of rows of the detectors, and acquiring a plurality of sampling points of the row of detectors on an extension line extending from an intersection point between the main detector arm support and the non-main detector arm support S22 — acquiring a plurality of intersection points respectively between lines connecting the target spot of the ray source with the plurality of sampling points and the plane formed by the non-main detector arm supports S23 — calculating detection values of the plurality of intersection points, according to a location of each detector pixel in the plane formed by the non-main detector arm supports and a detection value of the detector pixel, as detection values of the plurality of sampling points S24 — forming an image of the object under detection according to the detection values of the plurality of sampling points and a detection value of a detector on the main detector arm support

Fig. 10

DIGITAL RADIOGRAPHY SYSTEM AND DIGITAL RADIOGRAPHY METHOD

CROSS REFERENCE TO RELATED APPLICATION

The present application is a U.S. national stage filing under 35 U.S.C. § 371 from International Application No. PCT/CN2022/103739, filed on Jul. 4, 2022, and published as WO2023/280125 on Jan. 12, 2023, which claims priority to Chinese patent application No. 02110768526.4, entitled "DIGITAL RADIOGRAPHY SYSTEM AND DIGITAL RADIOGRAPHY METHOD", filed on Jul. 7, 2021, the entire contents of each of which are incorporated herein by reference.

TECHNICAL FIELD

The present disclosure relates to an object detection system, and more particularly to a digital radiography system and a digital radiography method.

BACKGROUND

Digital Radiography (DR) is a technology combining computer digital image processing technology and radiography technology. DR has advantages such as clear image, fast imaging and less radiation, and is widely used in the field of medical treatment and security inspection. DR's basic principle is that after the interaction of rays with an object, due to different physical properties of the object, amounts of the emitted rays arriving at detectors are different. According to the detected ray signals, a digital radiography projected image is formed.

In a conventional digital radiography system, a ray source and the detectors are located in a same plane, which is perpendicular to a transfer direction of the object. For example, the detectors are located in a folded line including a main detector arm support and a non-main detector arm support, and the ray source is arranged in a plane formed by the main detector arm support and the non-main detector arm support.

However, this configuration in which the ray source and the detectors are arranged in the same plane is unable to sufficiently utilize the ray source and the detectors. In addition, since the ray source and the detectors are required to be arranged in the same plane, the design of the digital radiography system is limited.

SUMMARY

The present disclosure provides a digital radiography system and a digital radiography method.

One aspect of the present disclosure provides a digital radiography system including: detectors mounted on a detector arm support formed in a first plane; and a ray source being non-coplanar with the first plane.

In the digital radiography system of the above aspect, the detector arm support includes a first detector arm support and at least one second detector arm support for mounting the detectors.

The digital radiography system of the above aspect further includes an image processing apparatus configured to acquire a corrected detection image according to a target spot of the ray source, locations of the first detector arm support and the second detector arm support, a moving speed of an object under detection, and detection values of the first detector arm support and the second detector arm support.

In the digital radiography system of the above aspect, the image processing apparatus includes: a projection acquisition portion configured to acquire projections of the target spot and the second detector arm support on a plane perpendicular to the first plane and a second plane formed by the target spot and the first detector arm support; a time deviation correction portion configured to acquire an angle between the first plane and the second plane using the projections on the plane perpendicular to the first plane and the second plane, and correct, according to the angle, a time deviation of detection data due to a distance by which the object under detection moves from the first plane to the second plane in a transfer direction; and a space deviation correction portion configured to perform space deviation correction on a detection value of a projection of each pixel on the second detector arm support on the second plane, and generate a final image of the object under detection based on the corrected detection value and the detection value of the first detector arm support.

In the digital radiography system of the above aspect, the time deviation correction portion includes: an angle calculation portion configured to calculate, using the plane perpendicular to the first plane and the second plane, an angle between the second detector arm support and a projected second detector arm support, in which the projected second detector arm support is a projection of the second detector arm support on the second plane in the transfer direction of the object under detection; a deviation ratio calculation portion configured to calculate, according to the angle, a preset equivalent height of the object under detection, and the moving speed of the object under detection, a ratio of a distance deviation between a detector on the second detector arm support and a projection of the detector with respect to a reference distance deviation between a detector on the second detector arm support at the equivalent height and a projection of the detector, in the transfer direction of the object under detection; and a detection data correction portion configured to correct, for a time sequence of detection data collected by the detector on the second detector arm support, a time deviation of the time sequence of the collected detection data according to the ratio and a time sampling period of a detector, so as to obtain corrected time deviation corrected data.

In the digital radiography system of the above aspect, the space deviation correction portion re-projects the projected second detector arm support onto a same straight line as the first detector arm support and acquires the final image of the object under detection.

In the digital radiography system of the above aspect, detection data at a time point other than sampling time is obtained by interpolation.

In the digital radiography system of the above aspect, the interpolation includes one of nearest neighbor interpolation, linear interpolation and quadratic interpolation.

The digital radiography system of the above aspect includes a plurality of rows of the detectors located in different planes, in which a plurality of second detector arm supports are located in a second plane.

In the digital radiography system of the above aspect, the image processing apparatus includes: a sampling point determination portion configured to select a row of detectors from the plurality of rows of the detectors and acquire a plurality of sampling points of the row of detectors on an extension line extending from an intersection point between the first detector arm support and the second detector arm support; an intersection point acquisition portion configured to acquire a plurality of intersection points respectively between lines connecting the target spot of the ray source with the plurality of sampling points and the second plane; a sampling point pixel value acquisition portion configured to calculate, according to a location of each detector pixel in the second plane and a detection value of the detector pixel, detection values of the plurality of intersection points as detection values of the plurality of sampling points; and an image acquisition portion configured to generate an image of the object under detection according to the detection values of the plurality of sampling points and a detection value of a detector on the first detector arm support.

In the digital radiography system of the above aspect, the image processing apparatus includes: a projection point determination portion configured to select a row of detectors from the plurality of rows of the detectors, and acquire, in a projection plane formed by the target spot of the ray source and the first detection arm support for the row of detectors, any point located in the projection plane at a side opposite to the first detector arm support with respect to the second plane and intersects the second plane as a projection point; an intersection point acquisition portion configured to acquire an intersection point between a line connecting the target spot with the projection point and the second plane; a projection point pixel value acquisition portion configured to calculate, according to a location of each detector pixel in the second plane and a detection value of the detector pixel, a detection value of the intersection point as a detection value of the projection point; and a corrected image acquisition portion configured to re-project the projection point onto a same straight line as the first detector arm support, and generate a corrected image of the object under detection according to a corrected detection value and a detection value of a detector on the first detector arm support for the row of detectors.

In the digital radiography system of the above aspect, the detection value of the intersection point is obtained by interpolation.

In the digital radiography system of the above aspect, the interpolation includes one of nearest neighbor interpolation, linear interpolation and quadratic interpolation.

In the digital radiography system of the above aspect, the farther the selected row of detectors away from the ray source, the greater an imaging range of the image of the object under detection.

In the digital radiography system of the above aspect, the sampling points are equally spaced or arbitrarily spaced.

In the digital radiography system of the above aspect, the plurality of rows of the detectors are equally spaced or unequally spaced.

In the digital radiography system of the above aspect, the detectors are arranged in a straight line or in an arc.

In the digital radiography system of the above aspect, under a condition that the detectors are arranged in an arc, the first detector arm support is a portion mounted with a single detector or a single module mounted with a plurality of detectors in a straight line.

The present disclosure further provides a digital radiography method applied to the above digital radiography system, including: a projection acquisition step, including acquiring projections of the target spot and the second detector arm support on a plane perpendicular to the first plane and a second plane formed by the target spot and the first detector arm support; a time deviation correction step, including acquiring an angle between the first plane and the second plane using the projections on the plane perpendicular to the first plane and the second plane, and correcting, according to the angle, a time deviation of detection data due to a distance by which the object under detection moves from the first plane to the second plane in a transfer direction; and a space deviation correction step, including performing space deviation correction on a detection value of a projection of each pixel on the second detector arm support on the second plane, and generating a final image of the object under detection based on the corrected detection value and the detection value of the first detector arm support.

In the above digital radiography method, the time deviation correction step includes: an angle calculation step, including calculating, using the plane perpendicular to the first plane and the second plane, an angle between the second detector arm support and a projected second detector arm support, in which the projected second detector arm support is a projection of the second detector arm support on the second plane in the transfer direction of the object under detection; a deviation ratio calculation step, including calculating, according to the angle, a preset equivalent height of the object under detection, and the moving speed of the object under detection, a ratio of a distance deviation between a detector on the second detector arm support and a projection of the detector with respect to a reference distance deviation between a detector on the second detector arm support at the equivalent height and a projection of the detector, in the transfer direction of the object under detection; and a detection data correction step, including correcting, for a time sequence of detection data collected by the detector on the second detector arm support, a time deviation of the time sequence of the collected detection data according to the ratio and a time sampling period of a detector, so as to obtain corrected time deviation corrected data.

In the above digital radiography method, the space deviation correction step further includes: re-projecting the projected second detector arm support onto a same straight line as the first detector arm support and acquiring the final image of the object under detection.

The present disclosure further provides a digital radiography method applied to the above digital radiography system, including: a sampling point determination step, including selecting a row of detectors from the plurality of rows of the detectors and acquiring a plurality of sampling points of the row of detectors on an extension line extending from an intersection point between the first detector arm support and the second detector arm support; an intersection point acquisition step, including acquiring a plurality of intersection points respectively between lines connecting the target spot of the ray source with the plurality of sampling points and the second plane; a sampling point pixel value acquisition step, including calculating, according to a location of each detector pixel in the second plane and a detection value of the detector pixel, detection values of the plurality of intersection points as detection values of the plurality of sampling points; and an image acquisition step, including generating an image of the object under detection according to the detection values of the plurality of sampling points and a detection value of a detector on the first detector arm support.

The present disclosure further provides a digital radiography method applied to the above digital radiography system, including: a projection point determination step, including selecting a row of detectors from the plurality of rows of the detectors, and acquiring, in a projection plane formed by the target spot of the ray source and the first detection arm support for the row of detectors, any point located in the projection plane at a side opposite to the first detector arm support with respect to the second plane and intersects the second plane as a projection point; an intersection point acquisition step, including acquiring an intersection point between a line connecting the target spot with the projection point and the second plane; a projection point pixel value acquisition step, including calculating, according to a location of each detector pixel in the second plane and a detection value of the detector pixel, a detection value of the intersection point as a detection value of the projection point; and a corrected image acquisition step, including re-projecting the projection point onto a same straight line as the first detector arm support, and generating a corrected image of the object under detection according to a corrected detection value and a detection value of a detector on the first detector arm support for the row of detectors.

BRIEF DESCRIPTION OF THE DRAWINGS

FIG. 5 shows a simplified schematic diagram of a non-main detector arm support, a projected non-main detector arm support, and a ray source as viewed from the X-axis direction;

FIG. 6 shows a flowchart of image processing of a digital radiography system according to Embodiment 1 of the present disclosure;

FIG. 9 shows a structural diagram of an image processing apparatus in a digital radiography system according to Embodiment 2 of the present disclosure;

FIG. 10 shows a flowchart of an image processing method for the digital radiography system according to Embodiment 2 of the present disclosure;

DETAILED DESCRIPTION

Features and exemplary embodiments of various aspects of the present disclosure will be described in detail below. In order to make the objects, technical solutions and advantages of the present disclosure clearer, the present disclosure will be further described in detail below with reference to the accompanying drawings and specific embodiments. It should be understood that the specific embodiments described herein are only configured to explain the present disclosure, but not to limit the present disclosure. For those skilled in the art, the present disclosure can be implemented without some of these specific details. The following description of the embodiments is merely to provide a better understanding of the present disclosure by illustrating the examples of the present disclosure.

The digital radiography system according to the present disclosure is described below in detail with reference to FIGS. 1 and 2. The digital radiography system according to the present disclosure includes: detectors mounted on a detector arm support formed in a first plane; and a ray source being non-coplanar with the first plane.

Figure 1:
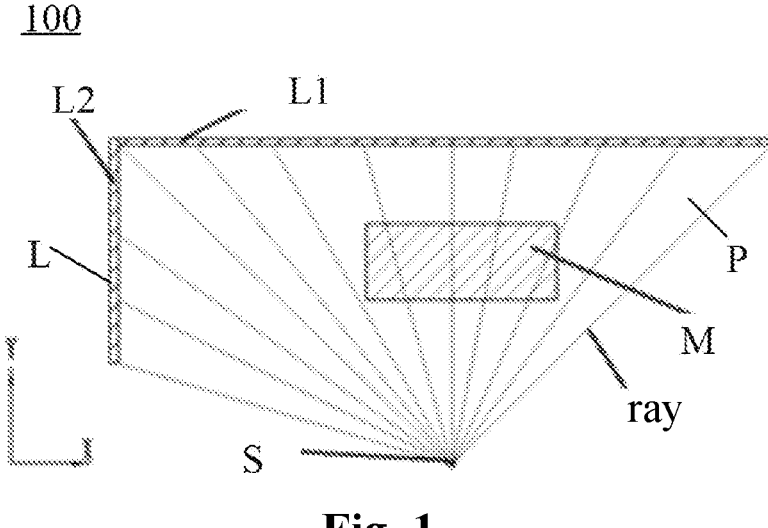
FIG. 1 shows a schematic diagram of a digital radiography system according to the present disclosure.

FIG. 1 shows a schematic diagram of a digital radiography system according to the present disclosure. The digital radiography system 100 includes a ray source S and detectors L. The detectors L are mounted on a main detector arm support L1 and a non-main detector arm support L2, and the main detector arm support L1 and the non-main detector arm support L2 form a plane P. The ray source may be a distributed ray source or a ray target spot source, and the following embodiments are described by taking the ray target spot source as an example. The ray source S is located outside the plane P, that is, the ray source S and the detectors L are located in different planes. The object under detection M is an object to be detected by ray scanning. Rays emitted by the ray source S are perpendicularly or obliquely incident onto and received by the detectors L.

Figure 2:
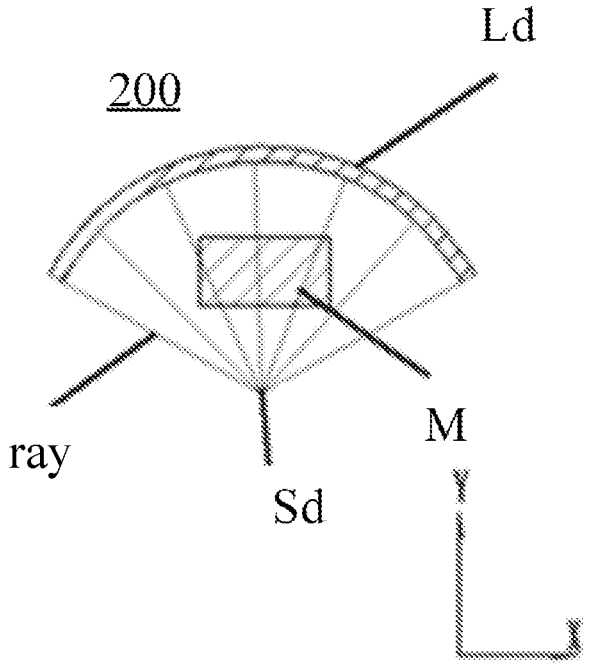
FIG. 2 shows a schematic diagram of another digital radiography system according to the present disclosure.

FIG. 2 shows a schematic diagram of another digital radiography system according to the present disclosure. The digital radiography system 200 includes a ray source Sd and detectors Ld. The detector arm support for the detectors Ld is formed as an arc, the ray source Sd is located outside the plane where the arc is located, and the ray source Sd and the detectors Ld are located in different planes.

Herein, the selection of the main detector arm support and the non-main detector arm support is relative, and if a certain detector arm support is selected as the main detector arm support, the remaining detector arm supports are all non-main detector arm supports. For example, in FIG. 1, L1 is the main detector arm support and L2 is the non-main detector arm support, and alternatively, L2 may be set as the main detector arm support and L1 may be set as the non-main detector arm support as required.

Therefore, in order to clearly imaging the object under detection, one or more sets of detectors that are non-coplanar with the ray source may be added to the original digital radiography system, and thus utilization of the ray source can be increased.

In addition, with the above arrangement, under a condition that the installation space for the digital radiography system is limited, the detectors and the ray source are not required to be arranged in a same plane, while the ray source may be arranged outside the plane where the detectors are located, and the flexibility for designing the digital radiography system is increased.

An image processing apparatus in the above digital radiography system is described below. Under a condition that the detectors located in a folded line or an arc are located in the same plane as the ray source, the detection image obtained directly according to the optical paths in this arrangement is generally deformed, and for example, the detection image may be compressed or stretched. This deformation is due to abrupt changes in projections of the detectors where the arm supports intersect. For solving this problem, the detection data of the detectors may be re-projected onto a straight line where the main detector is located by means of known space geometric correction. However, in the digital radiography system of the present disclosure, deformation of the image of the object under detection obtained according to the detection data cannot be corrected by means of space geometric correction. The inventor of the present disclosure has found the reason for this is that not only the object under detection is in different projection angles in terms of space, but also the projections of the object under detection are delayed in terms of time. As a result, the deformation of the object under detection cannot be solved simply by means of two-dimensional space geometric correction. The inventor of the present disclosure solves the above problems through both of space correction and time correction.

Embodiment 1

Figure 3:
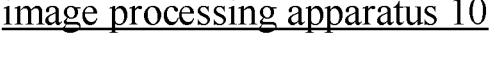
FIG. 3 shows a structural diagram of an image processing apparatus according to Embodiment 1 of the present disclosure.

FIG. 3 shows a schematic structural diagram of an image processing apparatus according to Embodiment 1 of the present disclosure. The image processing apparatus is configured to acquire a corrected image of the object under detection according to a target spot of the ray source, locations of the main detector arm support and the non-main detector arm support, a moving speed of the object under detection, and detection values of the main detector arm support and the non-main detector arm support. The image processing apparatus 10 includes a projection acquisition portion 101, a time deviation correction portion 102, and a space deviation correction portion 103.

Figure 4:
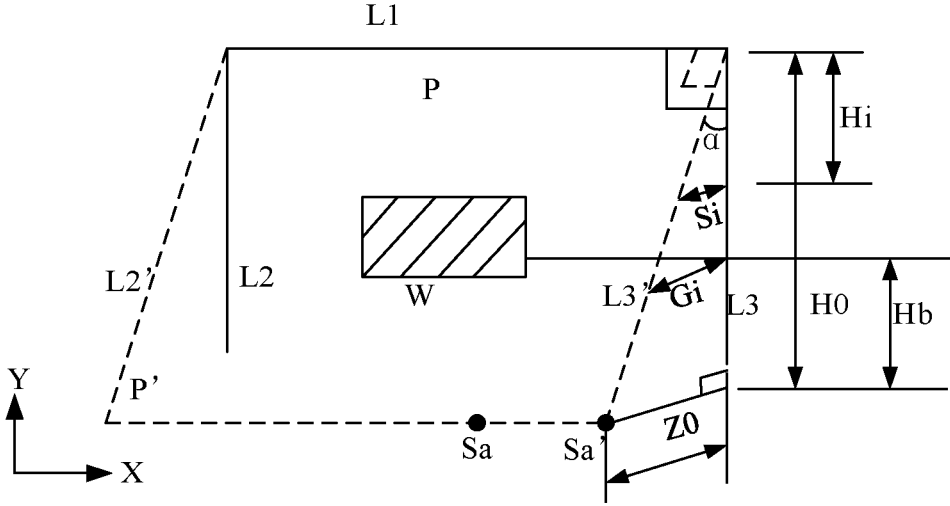
FIG. 4 shows a schematic diagram of acquiring projections in a digital radiography system according to the present disclosure.

FIG. 4 shows a schematic diagram of acquiring projections in a digital radiography system according to the present disclosure. For example, in FIG. 4, the main detector arm support L1 and the non-main detector arm supports L2, L3 form a plane P which is generally perpendicular to the ground (i.e., the plane P is located in a plane formed by an X-axis and a Y-axis in a rectangular coordinate system). A ray source Sa is located outside the plane P. The ray source Sa and the main detector arm support L1 form a plane P' other than the plane P, when the object under detection W moves along the transfer direction (i.e., a Z direction perpendicular to the X direction and the Y direction), the time at which the object under detection W receives rays when passing through the plane P and the plane P' are different, and thus the detection image may be bended due to such a time difference. In order to eliminate the bending, the deviation caused by the time difference should be eliminated. The inventor of the present disclosure proposes the following solution after discovering the above problem and its causes: projecting the non-main detector arm L2 onto the plane P', i.e., the plane P' formed by the ray source S and the main detector arm L1, so as to eliminate the time difference.

Firstly, the projection acquisition portion 101 is configured to acquire projections of the ray source Sa and the non-main detector arm support L2 (L3) on a plane perpendicular to the plane P and the plane P', in which the plane P' is formed by the ray source Sa and the main detector arm support L1.

FIG. 5 shows a simplified schematic diagram of a non-main detector arm support, a projected non-main detector arm support, and a ray source as viewed from the X-axis direction. Reference is made to FIGS. 4 and 5 below for illustration.

When determining the projections, the plane P' is formed by the ray source Sa and the main detector arm support L1. Since the main detector arm support L1 is located in the plane P', a detection value of the main detector arm support L1 is not required to be processed, and only the non-main detector arm supports L2 and L3 need to be projected onto the plane P', so as to eliminate, when the object under detection W is transferred along the direction Z perpendicular to the direction X and the direction Y, the time difference between the time at which the detector on the main detector arm support L1 receives the rays emitted by the ray source Sa and the time at which the detector on the non-main detector arm supports L2 and L3 receives the rays emitted by the ray source Sa. A projection of the non-main detector arm support L2 on the plane P' along the transfer direction of the object under detection W is referred to as a projected non-main detector arm support L2', and a projection of the non-main detector arm support L3 on the plane P' along the transfer direction of the object under detection W is referred to as a projected non-main detector arm support L3'. Herein, the non-main detector arm support L3 is taken as an example. Referring to FIG. 4, since the plane formed by the main detector arm support L1 and the non-main detector arm support L2 (L3) is generally arranged to be parallel to the coordinate XY plane, i.e., perpendicular to the ground, the non-main detector arm support L3 and the projected non-main detector arm support L3' herein form a plane perpendicular to both of the plane P and the plane P', and a projection of the ray source Sa on the plane perpendicular to both of the plane P and the plane P' is Sa'. That is, the plane perpendicular to both the plane P and the plane P' is a plane formed by the projection Sa' of the ray source and the non-main detector arm support L3.

In this way, after the projections are acquired by the projection acquisition portion 101, the time deviation correction portion 102 is configured to acquire an angle α between the plane P and the plane P' using the projections on the plane perpendicular to the plane P and the plane P', and correct, according to the angle α, a time deviation of detection data due to a distance by which the object under detection W moves from the plane P to the plane P' in the transfer direction Z.

Specifically, the time deviation correction portion 102 includes an angle calculation portion, a deviation ratio calculation portion, and a detection data correction portion.

Since a positional relationship between the detector arm support and the ray source is fixed after the digital radiography system is installed, in the perpendicular plane, a distance Z0 from the projection Sa' of the ray source to an extension line of the non-main detector arm support L3 and a distance H0 in a direction of the non-main detector arm support are known, and the angle calculation portion can calculate the angle α between the plane P and the plane P' using the following trigonometric function:

$$\alpha = \arctan\frac{Z0}{H0}.$$

Exemplarily, the distance Z0 is shown as a fixed value herein, but since the actual situation may be different, the distance Z0 may be alternatively shown as a variable parameter and determined according to image correction effect.

Next, the deviation ratio calculation portion is configured to calculate, according to the above calculated angle, an equivalent height of the object under detection, and the moving speed of the object under detection, a ratio of a distance deviation between a detector on the non-main detector arm support and a projection of the detector with respect to a distance deviation between a detector on the non-main detector arm support at the equivalent height and a projection of the detector, in the transfer direction of the object under detection W.

Herein, the equivalent height Hb of the object under detection W may be any height from a bottom height to a top height of the object under detection. Herein, the equivalent height refers to a vertical distance from a certain point of the object under detection W to the following plane: this plane refers to a plane that contains the ray source Sa and is parallel to the coordinate XZ plane. Therefore, the bottom height refers to a vertical distance from the bottom of the object under detection W to the above plane, and the top height refers to a vertical distance from the top of the object under detection W to the above plane.

Under a condition that $\alpha$ is determined, according to a position, Hi which is known, of each detector pixel i on the non-main detector arm support L3, a distance deviation Si between each detector pixel i on the non-main detector arm support L3 and the projected plane P' in the transfer direction of the object under detection W can be calculated by the following equation:

$$Si = Hi * \tan\alpha.$$

Exemplarily, the tangent function is used herein, but when the angle between the non-main detector arm support L3 and its projection is small, for example, 5 degrees or less, other trigonometric function values such as the sine value or the angle itself can be used for the calculation.

In addition, a distance deviation Gi of the object under detection W at the equivalent height Hb is determined, and Gi is a reference distance deviation. Under a condition that the transfer speed is fixed, the reference distance deviation Gi depends on the value of Hb. In this way, a ratio Si/Gi of the distance deviation Si between a detector on the non-main detector arm support and a projection of the detector with respect to the reference distance deviation Gi between a detector on the non-main detector arm support at the equivalent height Hi and a projection of the detector, in the transfer direction of the object under detection W, can be calculated. Under this condition, detection data at a time point other than sampling time points may be obtained by interpolation. The interpolation may include one of nearest neighbor interpolation, linear interpolation and quadratic interpolation.

Under a condition that the above ratio Si/Gi is acquired, the detection data correction portion is configured to correct, for a time sequence of image data collected by the detector on the non-main detector arm support, the time sequence of the collected detection data according to the above ratio Si/Gi and a time sampling period of a detector, so as to obtain corrected time deviation corrected detection data. As a result, the time deviation of the detection data is eliminated, and detection data located in different planes are projected onto a same plane, i.e., the plane P' in this embodiment.

It is assumed that a reading of the detector i in the time direction is r(t), and the time sampling period is T0.

Under a condition that the data at the detector i is delayed relative to the data at the main detector arm support, it is assumed that t1=ceil(Si/Gi), t2=floor(Si/Gi), and p=Si/Gi−t2, then:

$$r(t) = p * r(t - t1 * T0) + (1 - p) * r(t - t2 * T0),$$

in which the ceil function represents the smallest integer greater than a corresponding value, and the floor function represents the largest integer less than a corresponding value.

Under a condition that the data at the detector i is advanced relative to the data at the main detector arm support, t1=ceil(Si/Gi), t2=floor(Si/Gi), and p=Si/Gi−t2, then:

$$r(t) = p * r(t + t1 * T0) + (1 - p) * r(t + t2 * T0),$$

in which the ceil function represents the smallest integer greater than a corresponding value, and the floor function represents the largest integer less than a corresponding value.

Through the above processing, the sampled data r(t) can be delayed or advanced to eliminate deviations due to non-coplanarity of the detectors with the ray source.

The above processing is performed on each detector on the non-main detector arm support, so that the time deviations of detection values of all detectors on the non-main detector arm support can be corrected. Since the main detector arm support is located in the plane P', the processing is not required for the detection value of the detector on the main detector arm support. In this way, detection values of all detector pixels in the plane P' without time deviation can be acquired.

Due to abrupt changes in projections of the detectors where the arm supports intersect, the image formed from projections for the object under detection W may be compressed or stretched partially. Under this condition, the space deviation correction portion 103 is configured to re-project the projected second detector arm support, which is projected onto the plane P', onto a same straight line as the main detector arm support, so as to generate the final image of the object under detection W.

Known techniques may be employed for the space correction, and will not be repeated herein.

Through the above processing, the corrected image for the digital radiography system in which the ray source and the detectors are in different planes, i.e., not coplanar, can be obtained. In addition, according to the above processing, the deviations in terms of space and time of the detection image of the object under detection can be eliminated simultaneously, and an accurate image of the object under detection is obtained.

FIG. 6 shows a flowchart of image processing applied to the digital radiography system of Embodiment 1 of the present disclosure.

In step S11, projections of the target spot of the ray source and the non-main detector arm support on the perpendicular plane are acquired, in which the main detector arm support and the non-main detector arm support are mounted with detectors and located in the first plane, the target spot and the main detector arm support forms the second plane, and the perpendicular plane is perpendicular to the above first and second planes. In step S12, an angle between the non-main detector arm support and a projected detector arm support of this non-main detector arm support on the second plane is calculated. The angle is calculated using the trigonometric functions described above, which will not be repeated herein. In step S13, a distance difference Gi between a pixel on the non-main detector arm support at the equivalent height of the object under detection and a projection of the pixel in the transfer direction of the object under detection is determined. In step S14, a distance difference Si between each pixel on the non-main detector arm support and a projection of the pixel in the transfer direction of the object under detection is determined. In step S15, a ratio Si/Gi is determined. In step S16, time deviation correction is performed on the collected image data according to the ratio. In step S17, space deviation correction is performed on a detection value of a projection of each pixel on the non-main detector arm support on the second plane, and a final image of the object under detection is generated based on the corrected detection value and the detection value of the main detector arm support.

The image processing method for digital radiography is described above, and reference may be made to the description of the apparatus for the details of the method.

Embodiment 2

Next, Embodiment 2 of the image processing apparatus in the digital radiography system of the present disclosure is described with reference to FIGS. 7 and 8.

Embodiment 2 illustrates a digital radiography system in which the detectors and the target spot are not in a same plane and there are a plurality of rows of detector arm supports. FIG. 7 shows a schematic diagram of a digital radiography system in which a plurality of rows of detector arm supports mounted with detectors are non-coplanar with the target spot. FIG. 8 shows a side view of the digital radiography system shown in FIG. 7 as viewed from the X-axis direction.

The digital radiography system includes a ray source and a plurality of rows of detector arm supports which are non-coplanar with the ray source and located in different planes, and each row of the detector arm supports includes a main detector arm support and a non-main detector arm. Rays emitted by the ray source may be perpendicularly or obliquely incident on the detectors.

FIG. 9 shows a structural diagram of an image processing apparatus in the digital radiography system according to Embodiment 2 of the present disclosure. The image processing apparatus 20 according to Embodiment 2 includes: a sampling point determination portion 201 configured to select a row of detectors from a plurality of rows of detectors and acquire a plurality of sampling points of the row of detectors on an extension line extending from an intersection point between the main detector arm support and the non-main detector arm support; an intersection point acquisition portion 202 configured to acquire a plurality of intersection points respectively between lines connecting the position of the ray source with the plurality of sampling points and a plane formed by the non-main detector arm supports; a sampling point pixel value acquisition portion 203 configured to calculate, according to a location of each detector pixel in the plane formed by the non-main detector arm supports and a detection value of the detector pixel, detection values of the plurality of intersection points as detection values of the plurality of sampling points; and an image acquisition portion 204 configured to form a corrected image according to the detection values of the plurality of sampling points and a detection value of a detector on the first main detector arm support.

Figure 7:
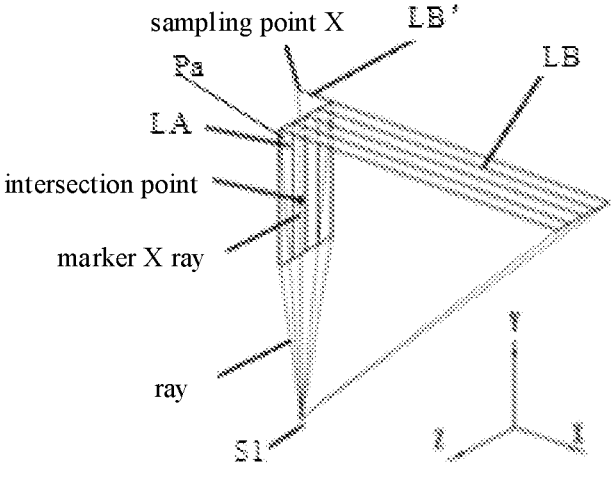
FIG. 7 shows a schematic diagram of a digital radiography system in which a plurality of rows of detector arm supports mounted with detectors are non-coplanar with a target spot.
Figure 8:
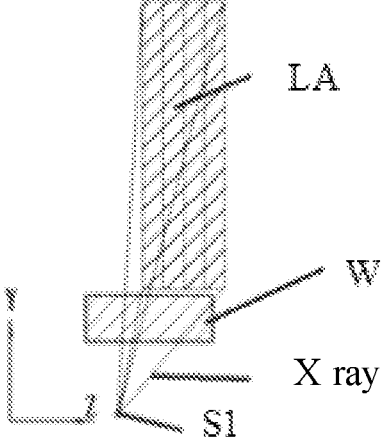
FIG. 8 shows a side view of the digital radiography system shown in FIG. 7 as viewed from the X-axis direction.

Reference is made to FIGS. 7 and 8 below for details. The digital radiography system in FIG. 7 includes a ray source S1 and a plurality of rows of detector arm supports. Each row of detector arm supports of the plurality of rows of detector arm supports includes a main detector arm support LB and a non-main detector arm support LA. The non-main detector arm supports LA constitute a non-main detector plane Pa.

The sampling point determination portion 201 is configured to select a row of detector arm supports from the plurality of rows of detector arm supports, the detector arm support at the outermost side is selected herein, and acquire a plurality of sampling points X of the row of detector arm supports on an extension line LB' extending from an intersection point between the main detector arm support LB and the non-main detector arm support LA, in which the coordinate of the sampling point X is (xi, yi, zi), and i=1, 2, 3, . . . . Herein, it is assumed that the plurality of sampling points X are equally spaced, but the plurality of sampling points X may be unequally spaced.

The intersection point acquisition portion 202 is configured to acquire the intersection points respectively between the lines connecting the ray source S1 with the sampling points X and the plane Pa, which is a plane where a plurality of rows of non-main detector arm supports are located. That is, the intersection point (xc, yc, zc) between a marker x ray and the plane Pa is determined according to the coordinate (sx, sy, sz) of the target spot of the ray source S1, the coordinate of the sampling point (xi, yi, zi), and the plane where the plurality of rows of non-main detector arm supports are located.

The sampling point pixel value acquisition portion 203 is configured to calculate, according to a location of each detector pixel in the plane Pa and a detection value of the detector pixel, detection values of the plurality of intersection points (xc, yc, zc) as detection values of the plurality of sampling points. Herein, the detection value at the intersection point (xc, yc, zc) is calculated, according to the detection value of each detector pixel in the plane Pa and the coordinate corresponding to the detector pixel, through interpolation as the reading of the projection point of the intersection point (xc, yc, zc), i.e., the detection value of the sampling point X. Herein, the interpolation may include one of nearest neighbor interpolation, linear interpolation and quadratic interpolation.

The image acquisition portion 204 is configured to form an image of the object under detection according to the detection values of the plurality of sampling points and a detection value of a detector on the main detector arm support LB.

Therefore, since the detection data from different planes are projected onto a same main detector arm support and its extension line, the acquired data is of high accuracy and the generated image is clearer.

In the selection of the detector arm supports, the detection value of each row of the detector arm supports may be used to obtain an image of the object under detection, and the farther the detector arm supports away from the target spot of the ray source, the greater an imaging range of the image of the object under detection. For the row of the detector arm supports closest to the target spot of the ray source, the imaging range of the object under detection is the smallest. Thus, an appropriate detector arm support may be selected as desired.

Through the above selection, the corrected and accurate image of the object under detection can still be obtained under a condition that a plurality of rows of the detectors are arranged.

An image processing method for the digital radiography system according to Embodiment 2 will be described below with reference to FIG. 10. FIG. 10 shows a flowchart of an image processing method for the digital radiography system of Embodiment 2 of the present disclosure. In step S21, a row of detectors is selected from the plurality of rows of the detectors, and a plurality of sampling points of the row of detectors on an extension line extending from an intersection point between the main detector arm support and the non-main detector arm support are acquired. In step S22, a plurality of intersection points respectively between lines connecting the target spot of the ray source with the plurality of sampling points and the plane formed by the non-main detector arm supports are acquired. In step S23, detection values of the plurality of intersection points are calculated, according to a location of each detector pixel in the plane formed by the non-main detector arm supports and a detection value of the detector pixel, as detection values of the plurality of sampling points. In step S24, an image of the object under detection is formed according to the detection values of the plurality of sampling points and a detection value of a detector on the main detector arm support. For the details of the image processing method, reference is made to the above description of the image processing apparatus.

Embodiment 3

Figure 11:
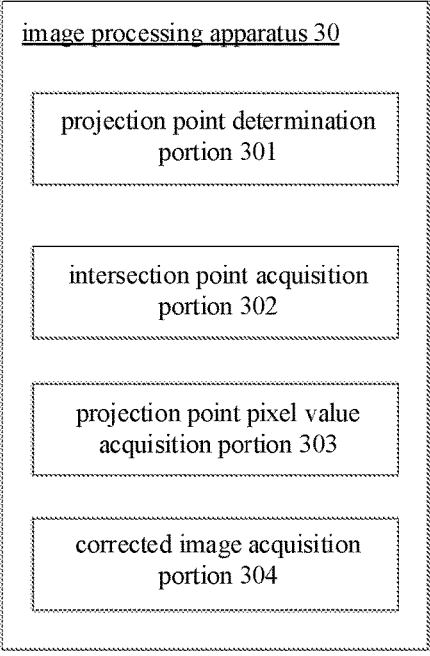
FIG. 11 shows a structural diagram of an image processing apparatus according to Embodiment 3 of the present disclosure.

The structure of the digital radiography system in Embodiment 3 is the same as the structure of the digital radiography system in Embodiment 2, and the difference lies only in the processing of the image processing apparatus. In the above Embodiment 2, the sampling points on the main detector arm support are directly acquired and used as the projection points to acquire the detection values corresponding to the sampling points. FIG. 11 shows a structural diagram of an image processing apparatus according to Embodiment 3 of the present disclosure. In the image processing apparatus 30, a projection point determination portion 301 is included in replace of the sampling point determination portion in Embodiment 2. The projection point determination portion 301 is configured to select a row of detectors from the plurality of rows of the detectors, and acquire, in a projection plane formed by the target spot of the ray source and the main detection arm support of the selected row of detectors, any point located in the projection plane at a side opposite to the main detector arm support LB with respect to the plane Pa and intersects the plane Pa as a projection point.

Actions performed by an intersection point acquisition portion 302 and a projection point pixel value acquisition portion 303 are the same as actions performed by the intersection point acquisition portion 202 and the sampling point pixel value acquisition portion 203 in Embodiment 2, and will not be repeated herein.

Finally, a corrected image acquisition portion 304 is configured to correct the detection value of the projection point and generate a corrected image of the object under detection according to a corrected detection value and a detection value of a detector on the main detector arm support for the row of detectors. In the above projection, the non-main detector arm support is projected onto the projection plane, i.e., the plane formed by the target spot and the main detector arm support, and according to Embodiment 1, this operation can eliminate the time deviation of the detection data. Space deviation correction is also necessary for the detection data, which is the same as the method mentioned in Embodiment 1, and will not be repeated herein.

Figure 12:
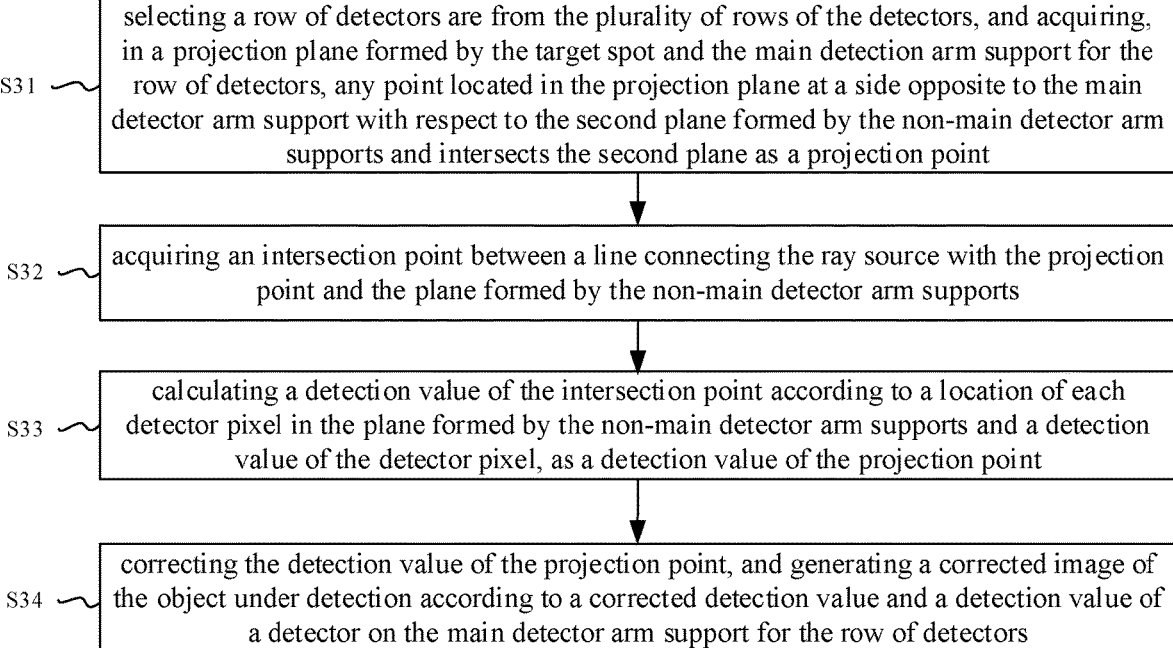
FIG. 12 shows a flowchart of an image processing method for the digital radiography system according to Embodiment 3.

FIG. 12 shows a flowchart of an image processing method for the image processing apparatus according to Embodiment 3. In step S31, a row of detectors is selected from the plurality of rows of the detectors, and in a projection plane formed by the target spot and the main detection arm support for the row of detectors, any point located in the projection plane at a side opposite to the main detector arm support with respect to the second plane formed by the non-main detector arm supports and intersects the second plane is acquired as a projection point. In step S32, an intersection point between a line connecting the ray source with the projection point and the plane formed by the non-main detector arm supports is acquired. In step S33, a detection value of the intersection point is calculated, according to a location of each detector pixel in the plane formed by the non-main detector arm supports and a detection value of the detector pixel, as a detection value of the projection point. In step S34, the detection value of the projection point is corrected, the projection point is re-projected onto a same straight line as the main detector arm support, and a corrected image of the object under detection is generated according to a corrected detection value and a detection value of a detector on the main detector arm support for the row of detectors.

The image processing apparatus in the digital radiography system has been described in detail above, but the present disclosure is not limited thereto.

In the above embodiments, the detector arm support is illustrated as a detector arm support in a folded line, but the detector arm support is not such limited and may be in an arc. The selection of the main detector arm is not limited and may be arbitrary. After the main detector arm support is determined, other detector arm supports are all non-main detector arm supports. For the detector arm support in an arc, the selection of the main detector arm support is determined by a detector module arranged in a straight line or a pixel. The detectors described above are arranged in a non-closed arrangement, but they may also be arranged in a closed arrangement.

In the above embodiments, a non-coplanar distribution with a single light source and a plurality of detector arm supports is described as an example, but a structure with a plurality of light sources and a single detector arm support or a structure with a plurality of light sources corresponding to a plurality of detector arm supports is also possible. In the above embodiments, the target spot of the ray source is described as an example, but a plurality of ray sources are also possible, such as a distributed ray source and a traditional optical machine. Such an arrangement is beneficial for reducing space and improving the utilization of the light source and the detectors.

Aspects of the present disclosure are described above with reference to flowcharts and/or block diagrams of methods, apparatuses (systems) and computer program products according to the embodiments of the present disclosure. It should be understood that each block in the flowchart and/or block diagram and a combination of the blocks in the flowchart and/or block diagram may be implemented by computer program instructions. These computer program instructions may be provided to a processor of a general-purpose computer, a specialized computer, or other programmable data processing device to produce a machine, so that these instructions, executed by the processor of the computers or other programmable data processing device, enable the implementation of the function/action specified in one or more blocks of the flowchart and/or block diagram. Such a processor may be, but is not limited to, a general purpose processor, a specialized processor, a special application processor, or a field programmable logic circuit. It should also be understood that each block in the block diagram and/or flowchart and a combination of the blocks in the block diagram and/or flowchart may also be implemented by specialized hardware that performs specified function or action, or by a combination of specialized hardware and computer instructions.

Although the implementations and the specific embodiments of the present disclosure are described above with reference to the drawings, various modifications and variations may be made by those skilled in the art without departing from the gist and scope of the present disclosure, and such modifications and variations fall within the scope defined by the appended claims.

What is claimed is:

1. A digital radiography system, comprising:
detectors mounted on a detector arm support formed in a first plane, wherein the detector arm support comprises a first detector arm support and at least one second detector arm support for mounting the detectors;
a ray source being non-coplanar with the first plane, wherein the detector arm support comprises a first detector arm support and at least one second detector arm support for mounting the detectors.

2. The digital radiography system according to claim 1, wherein the image processing apparatus comprises:
a projection acquisition portion configured to acquire projections of the target spot and the second detector arm support on a plane perpendicular to the first plane and a second plane formed by the target spot and the first detector arm support;
a time deviation correction portion configured to acquire an angle between the first plane and the second plane using the projections on the plane perpendicular to the first plane and the second plane, and correct, according to the angle, a time deviation of detection data due to a distance by which the object under detection moves from the first plane to the second plane in a transfer direction; and
a space deviation correction portion configured to perform space deviation correction on a detection value of a projection of each pixel on the second detector arm support on the second plane, and generate a final image of the object under detection based on the corrected detection value and the detection value of the first detector arm support.

3. The digital radiography system according to claim 2, wherein the time deviation correction portion comprises:
an angle calculation portion configured to calculate, using the plane perpendicular to the first plane and the second plane, an angle between the second detector arm support and a projected second detector arm support, wherein the projected second detector arm support is a projection of the second detector arm support on the second plane in the transfer direction of the object under detection;
a deviation ratio calculation portion configured to calculate, according to the angle, a preset equivalent height of the object under detection, and the moving speed of the object under detection, a ratio of a distance deviation between a detector on the second detector arm support and a projection of the detector with respect to a reference distance deviation between a detector on the second detector arm support at the equivalent height and a projection of the detector, in the transfer direction of the object under detection; and
a detection data correction portion configured to correct, for a time sequence of detection data collected by the detector on the second detector arm support, a time deviation of the time sequence of the collected detection data according to the ratio and a time sampling period of a detector, so as to obtain corrected time deviation corrected data.

4. The digital radiography system according to claim 3, wherein
the space deviation correction portion re-projects the projected second detector arm support onto a same straight line as the first detector arm support and acquires the final image of the object under detection.

5. The digital radiography system according to claim 3, wherein
detection data at a time point other than sampling time is obtained by interpolation.

6. The digital radiography system according to claim 5, wherein
the interpolation comprises one of nearest neighbor interpolation, linear interpolation and quadratic interpolation.

7. The digital radiography system according to claim 1, comprising:
a plurality of rows of the detectors located in different planes,
wherein a plurality of second detector arm supports are located in a second plane.

8. The digital radiography system according to claim 7, wherein the image processing apparatus comprises:
a sampling point determination portion configured to select a row of detectors from the plurality of rows of the detectors and acquire a plurality of sampling points of the row of detectors on an extension line extending from an intersection point between the first detector arm support and the second detector arm support;
an intersection point acquisition portion configured to acquire a plurality of intersection points respectively between lines connecting the target spot of the ray source with the plurality of sampling points and the second plane;
a sampling point pixel value acquisition portion configured to calculate, according to a location of each detector pixel in the second plane and a detection value of the detector pixel, detection values of the plurality of intersection points as detection values of the plurality of sampling points; and
an image acquisition portion configured to generate an image of the object under detection according to the detection values of the plurality of sampling points and a detection value of a detector on the first detector arm support.

9. The digital radiography system according to claim 8, wherein
the detection value of the intersection point is obtained by interpolation, and the interpolation comprises one of nearest neighbor interpolation, linear interpolation and quadratic interpolation.

10. The digital radiography system according to claim 8, wherein
the farther the selected row of detectors away from the ray source, the greater an imaging range of the image of the object under detection.

11. The digital radiography system according to claim 8, wherein
the sampling points are equally spaced or arbitrarily spaced.

12. The digital radiography system according to claim 8, wherein
the plurality of rows of the detectors are equally spaced or unequally spaced.

13. The digital radiography system according to claim 7, wherein the image processing apparatus comprises:

a projection point determination portion configured to select a row of detectors from the plurality of rows of the detectors, and acquire, in a projection plane formed by the target spot of the ray source and the first detection arm support for the row of detectors, any point located in the projection plane at a side opposite to the first detector arm support with respect to the second plane and intersects the second plane as a projection point;

an intersection point acquisition portion configured to acquire an intersection point between a line connecting the target spot with the projection point and the second plane;

a projection point pixel value acquisition portion configured to calculate, according to a location of each detector pixel in the second plane and a detection value of the detector pixel, a detection value of the intersection point as a detection value of the projection point; and a corrected image acquisition portion configured to re-project the projection point onto a same straight line as the first detector arm support, and generate a corrected image of the object under detection according to a corrected detection value and a detection value of a detector on the first detector arm support for the row of detectors.

14. A digital radiography method applied to the digital radiography system according to claim 7, comprising:

a projection point determination step, comprising selecting a row of detectors from the plurality of rows of the detectors, and acquiring, in a projection plane formed by the target spot of the ray source and the first detection arm support for the row of detectors, any point located in the projection plane at a side opposite to the first detector arm support with respect to the second plane and intersects the second plane as a projection point;

an intersection point acquisition step, comprising acquiring an intersection point between a line connecting the target spot with the projection point and the second plane;

a projection point pixel value acquisition step, comprising calculating, according to a location of each detector pixel in the second plane and a detection value of the detector pixel, a detection value of the intersection point as a detection value of the projection point; and a corrected image acquisition step, comprising re-projecting the projection point onto a same straight line as the first detector arm support, and generating a corrected image of the object under detection according to a corrected detection value and a detection value of a detector on the first detector arm support for the row of detectors.

15. The digital radiography system according to claim 1, wherein the detectors are arranged in a straight line or in an arc.

16. The digital radiography system according to claim 15, wherein under a condition that the detectors are arranged in an arc, the first detector arm support is a portion mounted with a single detector or a single module mounted with a plurality of detectors in a straight line.

17. A digital radiography method applied to the digital radiography system according to claim 1, comprising:

a projection acquisition step, comprising acquiring projections of the target spot and the second detector arm support on a plane perpendicular to the first plane and a second plane formed by the target spot and the first detector arm support;

a time deviation correction step, comprising acquiring an angle between the first plane and the second plane using the projections on the plane perpendicular to the first plane and the second plane, and correcting, according to the angle, a time deviation of detection data due to a distance by which the object under detection moves from the first plane to the second plane in a transfer direction; and a space deviation correction step, comprising performing space deviation correction on a detection value of a projection of each pixel on the second detector arm support on the second plane, and generating a final image of the object under detection based on the corrected detection value and the detection value of the first detector arm support.

18. A digital radiography method applied to the digital radiography system according to claim 7, comprising:

a sampling point determination step, comprising selecting a row of detectors from the plurality of rows of the detectors and acquiring a plurality of sampling points of the row of detectors on an extension line extending from an intersection point between the first detector arm support and the second detector arm support;

an intersection point acquisition step, comprising acquiring a plurality of intersection points respectively between lines connecting the target spot of the ray source with the plurality of sampling points and the second plane;

a sampling point pixel value acquisition step, comprising calculating, according to a location of each detector pixel in the second plane and a detection value of the detector pixel, detection values of the plurality of intersection points as detection values of the plurality of sampling points; and an image acquisition step, comprising generating an image of the object under detection according to the detection values of the plurality of sampling points and a detection value of a detector on the first detector arm support.

\* \* \* \* \*